US012709630B2

(12) United States Patent
Nash

(10) Patent No.: US 12,709,630 B2
(45) **Date of Patent: *Aug. 18, 2026**

(54) ADVANCED GLYCATION END PRODUCT ANALOGUES

(71) Applicant: Phytoquest Limited, Aberystwyth (GB)

(72) Inventor: Robert James Nash, Ystrad-Meurig (GB)

(73) Assignee: Phytoquest Limited, Aberystwyth (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/598,200

(22) Filed: Mar. 7, 2024

(65) Prior Publication Data

US 2024/0360171 A1 Oct. 31, 2024

Related U.S. Application Data

(60) Division of application No. 16/990,890, filed on Aug. 11, 2020, now Pat. No. 11,970,513, which is a continuation of application No. 15/832,028, filed on Dec. 5, 2017, now abandoned, which is a continuation of application No. 14/410,053, filed as application No. PCT/GB2013/000279 on Jun. 25, 2013, now abandoned.

(30) Foreign Application Priority Data

Jun. 26, 2012 (GB) ..................................... 1211271

(51) Int. Cl.

| | |
|---|---|
| ***A61K 36/00*** | (2006.01) |
| ***A61K 36/19*** | (2006.01) |
| ***A61K 36/23*** | (2006.01) |
| ***A61K 36/28*** | (2006.01) |
| ***A61K 36/38*** | (2006.01) |
| ***A61K 36/66*** | (2006.01) |
| ***A61K 36/81*** | (2006.01) |
| ***A61K 36/87*** | (2006.01) |
| ***C07H 7/02*** | (2006.01) |
| ***G01N 30/06*** | (2006.01) |
| ***G01N 30/72*** | (2006.01) |
| ***G01N 33/68*** | (2006.01) |
| ***H01J 49/00*** | (2006.01) |

(52) U.S. Cl.

CPC ............... *C07H 7/02* (2013.01); *A61K 36/19* (2013.01); *A61K 36/23* (2013.01); *A61K 36/28* (2013.01); *A61K 36/38* (2013.01); *A61K 36/66* (2013.01); *A61K 36/81* (2013.01); *A61K 36/87* (2013.01); *G01N 30/06* (2013.01); *G01N 30/7206* (2013.01); *G01N 33/6806* (2013.01); *H01J 49/0027* (2013.01)

(58) Field of Classification Search

None

See application file for complete search history.

(56) References Cited

U.S. PATENT DOCUMENTS

| | | |
|---|---|---|
| 6,004,958 A | 12/1999 | Brown et al. |
| 7,109,309 B2 | 9/2006 | Shigetoh et al. |
| 11,970,513 B2 | 4/2024 | Nash |
| 2006/0241023 A1 | 10/2006 | Brown et al. |
| 2007/0065443 A1 | 3/2007 | Tobia et al. |
| 2015/0191501 A1 | 7/2015 | Nash |
| 2018/0094013 A1 | 4/2018 | Nash |
| 2021/0054012 A1 | 2/2021 | Nash |

FOREIGN PATENT DOCUMENTS

WO WO 01/35972 A1 5/2001

OTHER PUBLICATIONS

International Search Report and Written Opinion for Application No. PCT/GB2013/000279 mailed Sep. 12, 2013.

International Preliminary Report on Patentability for Application No. PCT/GB2013/000279, mailed Jan. 8, 2015.

[No Author Listed] Database WPI, AN 2001-270603 XP002712143, & JP 2001 057897 A (Daiichi Kakagu Yakuhin KK) Abstract. Week Feb. 8, 2001. Thomson Scientific, London, GB. Mar. 6, 2001. 2 Pages.

[No Author Listed] Database WPI, AN 2009-B41685 XP002712130, & JP 2009 000084 A (Toyobo KK) Abstract. Week Jan. 2, 2009. Thomson Scientific, London, GB. Jan. 8, 2009. 1 Page.

Ashoor et al., Maillard browning of common amino acids and sugars. J Food Science. 1984;49:1206-7.

Barnes et al., St John's wort (*Hypericum perloratum* L.): a review of its chemistry, pharmacology and clinical properties. J Pharm Pharmacol. May 2001;53(5):583-600. doi: 10.1211/0022357011775910.

Chen et al., Antioxidant and anti-inflammatory activities of Maillard reaction products isolated from sugar-amino acid model systems. J Agric Food Chem. Oct. 26, 2011;59(20):11294-303. doi: 10.1021/jf2031583. Epub Oct. 4, 2011.

Chen et al., Comparison of volatile generation in serine/threonine/glutamineribose/glucose/fructose model systems. J Agric Food Chem. Feb. 1999;47(2):643-7.

Dills et al., Protein fructosylation: fructose and the Maillard reaction. Am J Clin Nutr. Nov. 1993;58(5 Suppl):779S-787S. Review.

Hwang et al., Biological activities of Maillard reaction products (MRPs) in a sugar-amino acid model system. Food Chem. 2011;126:221-7.

Ide et al., Antioxidant effects of fructosyl arginine, a Maillard reaction product in aged garlic extract. J Nutr Biochem. Jun. 1999;10(6):372-6. doi: 10.1016/s0955-2863(99)00021-2.

(Continued)

*Primary Examiner* — Russell G Fiebig

(74) *Attorney, Agent, or Firm* — Wolf, Greenfield & Sacks, P.C.

(57) ABSTRACT

Disclosed are processes for the production of composition comprising one or more fructose amino acids, said process comprising the steps of: (a) providing plant material derived from a botanical source selected from plants of the families Solanaceae, Compositae, (Asteraceae), Guttiferae, Umbelliferae, Papaveraceae, Vitidaceae or Acanthaceae; (b) extracting one or more fructose amino acid(s) from said plant material; and optionally (c) detecting the presence and/or measuring the amount of said fructose amino acid(s) in the extract of step (b).

5 Claims, 1 Drawing Sheet

(56) References Cited

OTHER PUBLICATIONS

Mccance et al., Maillard reaction products and their relation to complications in insulin-dependent diabetes mellitus. J Clin Invest. Jun. 1993;91(6):2470-8.

Mossine et al., Antitumor effects of the early maillard reaction products. Royal Society of Chemistry. 2010;322 (Maillard Reaction):170-9.

Mossine et al., The preparation and characterization of some Amadori compounds (1-amino-1-deoxy-D-fructose derivatives) derived from a series of aliphatic omega-amino acids. Carbohydr Res. Sep. 15, 1994;262(2):257-70.

O'Brien et al., Nutritional and toxicological aspects of the maillard browning reaction in foods. Critical Reviews in Food Science and Nutrition. 2009;28(3):211-48.

Oimomi et al., Increased fructose-lysine of hair protein and blood glucose control in diabetic patients. Horm Metab Res. Oct. 1988;20(10):654-5.

Ozturk et al., Wound-healing activity of St. John's Wort (*Hypericum perforatum* L.) on chicken embryonic fibroblasts. J Ethnopharmacol. Apr. 20, 2007;111(1):33-9. doi: 10.1016/j.jep.2006.10.029. Epub Nov. 6, 2006.

Roper et al., N.M.R. Spectroscopy of N-(1-Deoxy-D-Fructos-1-YL)-L-Amino acids ("fructose-amino acids"). Carbohydrate Res. 1983;116:163-95.

Schempp et al., Topical treatment of atopic dermatitis with St. John's wort cream—a randomized, placebo controlled, double blind half-side comparison. Phytomedicine. 2003;10 Suppl 4:31-7. doi: 10.1078/1433-187x-00306.

Sgarbieri et al., Nutritional consequences of the Maillard reaction. Amino acid availability from fructose-leucine and fructose-tryptophan in the rat. J Nutr. May 1973;103(5):657-63.

Vhangani et al., Antioxidant activity of Maillard reaction products (MRPs) derived from fructoselysine and ribose-lysine model systems. Food Chem. Apr. 15, 2013;137(1-4):92-8. doi: 10.1016/j.foodchem.2012.09.030. Epub Sep. 16, 2012.

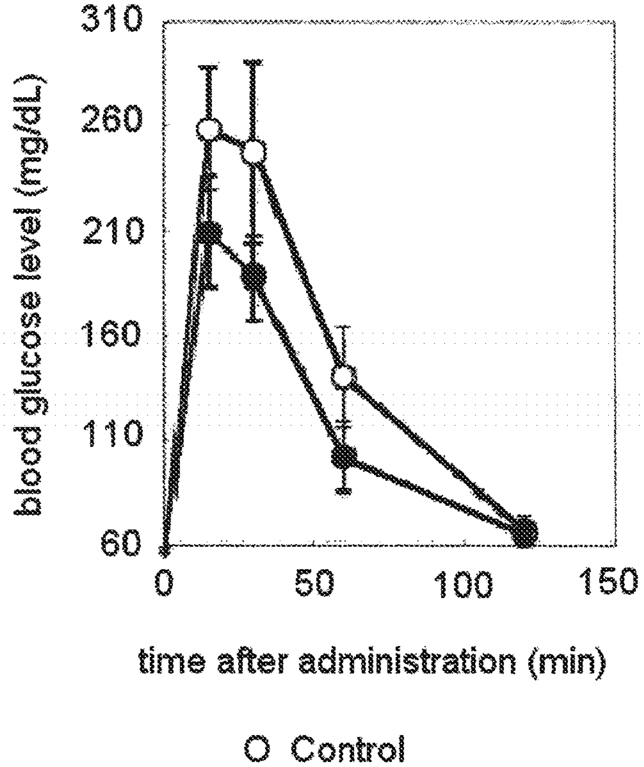
310
260
210
160
110
60
blood glucose level (mg/dL)
0
50
100
150
time after administration (min)
Control
900156

ADVANCED GLYCATION END PRODUCT ANALOGUES

RELATED APPLICATIONS

This application is a division of U.S. application Ser. No. 16/990,890, filed Aug. 11, 2020, pending, which is a continuation of U.S. application Ser. No. 15/832,028, filed Dec. 5, 2017, abandoned, which is a continuation of U.S. application Ser. No. 14/410,053, filed Dec. 19, 2014, abandoned, which is a national stage filing under 35 U.S.C. § 371 of International Application No. PCT/GB2013/000279 with an international filing date of Jun. 25, 2013, which claims the benefit of Great Britain Patent Application Serial No. 1211271.0 filed Jun. 26, 2012, the entire contents of each of which are incorporated by reference herein.

FIELD OF THE INVENTION

This invention relates to certain advanced glycation end product analogues for treating AGE-mediated diseases such as diabetes, diabetic cataracts, atherosclerosis, diabetic nephropathy and neurodegenerative diseases (including Alzheimer's disease, Parkinson's disease), amyotrophic lateral sclerosis (ALS or Lou Gehrig's disease) and depression. The Invention also finds application in methods for the treatment of Inflammatory diseases and for reducing inflammation caused by advanced glycation end products.

The invention also relates to methods for monitoring the quality of products containing fructose amino acids produced from plants including *Hypericum performatum* (St John's wort), *Cissus* species, *Andrographis paniculata, Stevie rebaudiana, Solanum tuberosum, Conopodium species, Panax ginseng, Angelica archangelica, Angelica sinensis, Sanguinara canadensis, Lycium* species and *Matricaria chamomila* (chamomile) as well as to extracts obtainable by such processes.

BACKGROUND OF THE INVENTION

The active components of most herbal products are not known. It has now been discovered that several herbal products and food/beverage ingredients contain fructose amino acids which can be considered as analogues of mammalian advanced glycation end products (AGEs), or in some cases are the same structures.

Although fructose amino acids have been Identified in a few plants previously (for example, fructosyl arginine in *Panax ginseng*), their identification and correlation with biological activity of herbal products such as those from St John's wort has not been reported.

Glycation (nonenzymatic glycosylation) processes, also known as the Maillard reactions, are a series of reactions between carbohydrates and free amino groups of proteins. The preliminary Intermediates (Amadori products; 1-amino, 1-deoxy, 2-ketoses), ultimately result in the formation of AGEs.

AGEs in humans have been predominantly chemically characterized by the detection of pentosidine and N-carboxy-methyl lysine (CML). The formation of AGEs progressively increases with normal ageing of mammals, even in the absence of disease.

Under certain pathologic conditions (e.g., oxidative stress due to hyperglycaemia in diabetics), AGE formation can be Increased beyond normal levels. AGEs are now known to also play a role as proinflammatory mediators in gestational diabetes, and the formation and accumulation of advanced glycation end products (AGEs) has also been implicated in the progression of age-related diseases. AGEs have also been implicated in Alzheimer's Disease, cardiovascular disease, and stroke. Reduced muscle function is also associated with AGEs.

AGEs interact with cell surface receptors that may have homeostatic function by clearing/detoxifying AGE-modified macromolecules from serum and tissues. However, a major consequence of activation of the receptor for AGE (RAGE) is to evoke downstream pro-inflammatory responses that could play a critical role in age-related diseases. Besides RAGE, there are other receptors which are believed to bind advanced glycation end products.

Diseases that have been linked to RAGE include:

Atherosclerosis
Peripheral vascular disease
Myocardial infarction
Congestive heart failure
Diabetic retinopathy
Diabetic neuropathy
Diabetic nephropathy
Alzheimer's disease
Psoriasis However, these receptors could play a role in removal of AGE rather than in signal transduction (as is the case for RAGE).

We have now discovered that several plant products with claimed clinical benefits in diseases such as diabetes contain appreciable concentrations of analogues of AGEs.

Without wanting to be bound by theory we propose that these compounds on consumption Interact with AGE receptors leading to decreases in Inflammatory responses or may lead to increased removal of metabolic AGEs.

Without wishing to be bound by theory we further propose that these compounds can give protection or relief from depression due to inhibition of glycosidases such as hexosaminidase and beta-glucuronidase elevated in depression and many other disorders including diabetes mellitus, granuloma annulare and HIV. These enzyme activities are also elevated in neurological disorders such as epileptic seizure and hexosaminidases can be deposited in Alzheimer's disease. Glycosidase inhibitors are know under certain circumstances to act as pharmacological chaperones (see Nash et al., 2011, Future Medicinal Chemistry, Vol. 3, Pages 1513-1521 and references therein) and so we also propose that fructose amino acids from plants can improve the function of certain glycosidase enzymes and perhaps prevent deposition. The presence of AGE analogues in St John's wort products has not been reported by other workers even though they are major components. St John's wort is known to provide clinical benefits in depression but the active components have remained a matter of scientific debate.

AGE analogues constitute a widely distributed class of phytochemicals that have escaped previous serious clinical investigation. Thus, the discovery that the botanical distribution of the AGE analogues correlates with medicinal plants used for the treatment of various diseases is of great significance.

SUMMARY OF THE INVENTION

The present invention is based, at least in part, on the surprising discovery that the botanical distribution of certain analogues of human advanced glycation end products (AGEs) correlates with medicinal plants used for the treatment of diabetes, depression and inflammatory diseases.

These phytochemical AGE analogues have utility as agonists and antagonists of AGE receptors and have additional medicinal properties through inhibition of glucuronidase and hexosaminidases (both of which are elevated in various diseases including metabolic syndrome, Alzheimer's and depression). For the first time, fructo-amino acid conjugates have been Identified as important bioactive principles in established herbal medicines such as St John's wort and chamomile.

Thus, according to the invention there is provided a composition comprising an isolated fructose amino acid for use in therapy or prophylaxis (embodiment 1).

Other embodiments are listed below:

Embodiment 2. A cosmetic, nutraceutical or pharmaceutical composition, or herbal medicine, comprising an isolated fructose amino acid, optionally further comprising a cosmetically-, nutraceutically- or pharmaceutically-acceptable excipient or carrier.

Embodiment 3. A method for treating AGE-mediated disease in a subject in need thereof, comprising administering an effective amount of a composition comprising an isolated fructose amino acid to said subject.

Embodiment 4. A cosmetic method for Improving the appearance of the skin comprising the step of applying a composition comprising an isolated fructose amino acid to the skin.

Embodiment 5. Use of a fructose amino acid for the manufacture of a medicament for the treatment of AGE-mediated disease.

Embodiment 8. The composition, method or use of any one of the preceding embodiments wherein the fructose amino acid is synthetic or purified from a botanical source.

Embodiment 7. A process for the production of composition comprising one or more fructose amino acids, said process comprising the steps of:

(a) providing plant material;

(b) extracting one or more fructose amino acid(s) from said plant material; and then (c) formulating said fructose amino acids with a cosmetically-, nutraceutically- or pharmaceutically-acceptable excipient or carrier to produce a composition in which the amount and concentration of the extracted fructose amino acids is sufficient to treat AGE-mediated disease in a subject.

Embodiment 8. A process for producing a cosmetic, nutraceutical or pharmaceutical composition, or herbal medicine, comprising the step of monitoring the quality of said cosmetic, nutraceutical or pharmaceutical composition, or herbal medicine, by detecting the presence or absence or measuring the amount of a fructose amino acid in a sample of said cosmetic, nutraceutical or pharmaceutical composition, or herbal medicine.

Embodiment 9. A method for monitoring the quality of a cosmetic, nutraceutical or pharmaceutical composition, or herbal medicine, comprising the steps of (a) providing a sample of the cosmetic, nutraceutical or pharmaceutical composition, or herbal medicine; and (b) detecting the presence or absence or measuring the amount of a fructose amino acid in said sample.

Embodiment 10. A process for producing a supplemented cosmetic, foodstuff or beverage comprising the steps of:

(a) providing a herbal medicine or nutraceutical;

(b) monitoring the quality of said herbal medicine or nutraceutical of step (a) according to the method of embodiment 9; and (c) adding the herbal medicine or nutraceutical to a cosmetic, foodstuff or beverage to produce said supplemented cosmetic, foodstuff or beverage.

Embodiment 11. The process or method of any one of embodiments 7-10 wherein the cosmetic, nutraceutical or pharmaceutical composition, herbal medicine or sample is derived from a botanical source.

Embodiment 12. The composition, process, method or use of embodiment 6 or embodiment 11 wherein the botanical source comprises plants of the families Solanaceae, Compositae (Asteraceae), Guttiferae, Umbelliferae, Papaveraceae, Araliaceae, Vitidaceae or Acanthaceae.

Embodiment 13. The composition, process, method or use of embodiment 12 wherein the botanical source comprises plants of the genera *Hypericum, Lycium, Cissus, Matricaria, Stevia, Angelica, Sanguinaria, Andrographis, Solanum, Panax* or *Conopodium.*

Embodiment 14. The composition, process, method or use of embodiment 13 wherein the botanical source comprises plants of the species *Hypericum perforatum.*

Embodiment 15. The composition, process, method or use of embodiment 12 wherein the botanical source comprises Solanaceae fruit, for example Goji berries (*Lycium*), or tubers, for example potatoes.

Embodiment 16. The composition, process, method or use of embodiment 13 wherein the botanical source comprises fruits, flowers, roots or leaves from plants of *Stevia rebaudiana.*

Embodiment 17. The composition, process, method or use of embodiment 13 wherein the botanical source comprises fruits, flowers, roots or leaves from plants of *Matricaria chamomilia.*

Embodiment 18. The composition, method, process or use of any one of the preceding embodiments wherein the isolated fructose amino acid is present in the composition at a level of at least: 5% w/w, 10% w/w; 15% w/w 20% w/w; 25% w/w; 30% w/w; 35% w/w; 40% w/w; 45% w/w; 50% w/w, 60% w/w, 70% w/w, 80% w/w, 90% w/w, 99% w/w (on a dry weight basis).

Embodiment 19. A composition obtainable by the process of any one of embodiments 7-8 or 10-18 for the treatment of AGE-mediated disease.

Embodiment 20. A combination comprising (or consisting essentially of): (a) an anti-diabetic, anti-depressant or anti-inflammatory agent; and (b) a fructose amino acid, for example an isolated fructose amino acid.

Embodiment 21. A pharmaceutical pack, kit or patient pack comprising a combination as defined in embodiment 20.

Embodiment 22. An anti-diabetic, anti-depressant or anti-inflammatory agent for use in combination therapy with a fructose amino acid, for example an isolated fructose amino acid.

Embodiment 23. A fructose amino acid, for example an isolated fructose amino acid, for use in combination therapy with an anti-diabetic, anti-depressant or anti-inflammatory agent.

Embodiment 24. The anti-diabetic, anti-depressant or anti-inflammatory agent of embodiment 22 or fructose amino acid of embodiment 23 wherein the combination therapy comprises the treatment of AGE-mediated disease.

Embodiment 25. The combination, pack or kit of embodiment 20 or 21 wherein the anti-depressant, anti-diabetic or anti-inflammatory agent is selected from: (a) a steroid; (b) a non-steroidal anti-inflammatory drug (NSAID); and (c) an immune selective anti-inflammatory derivative (ImSAID) or (d) iminosugar.

Embodiment 26. The composition, method, process or use of any one of the preceding embodiments wherein said AGE-mediated disease is selected from: inflammatory diseases; depression; neurodegenerative disorders, including Alzheimer's disease and Parkinson's disease; diabetes; complications and clinical sequelae of diabetes; amyotrophic lateral sclerosis (ALS or Lou Gehrig's disease); muscle wasting; atherosclerosis; peripheral vascular disease: myocardial infarction; congestive heart failure; diabetic cataracts; diabetic retinopathy; diabetic neuropathy; diabetic nephropathy; ageing, swelling or erythema of the skin and psoriasis.

Embodiment 27. The composition, method, process or use of embodiment 26 wherein said AGE-mediated disease is selected from: autoimmune disease, asthma, allergy, graft versus host disease; sarcoidosis; vascular inflammatory disease, including disseminated intravascular coagulation, atherosclerosis, Kawasaki's pathology; vasculitis; Sjogren's syndrome; psoriatic arthritis; enteropathic arthritis; reactive arthritis and arthritis associated with inflammatory bowel disease.

Embodiment 28. The composition, method, process or use of embodiment 27 wherein said autoimmune disease is selected from: Grave's disease; rheumatoid arthritis; Hashimoto's thyroiditis; vitiligo; diabetes (e.g. type I diabetes or type II diabetes); pernicious anaemia; multiple sclerosis; glomerulonephritis; systemic lupus E (SLE, lupus); Sjogren syndrome; scleroderma; psoriasis; ankylosing spondilitis; myasthenia gravis; pemphigus; polymyositis; dermomyositis; uveitis; Guillain-Barre syndrome; Crohn's disease; ulcerative colitis and inflammatory bowel disease (IBD).

Embodiment 29. The composition, method, process or use of embodiment 27 wherein said allergy is selected from: atopic allergy, allergic rhinitis, allergic conjunctivitis, atopic dermatitis, hypereosinophilia, irritable bowel syndrome, allergen-induced migraine, bacterial allergy, bronchial allergy (asthma), contact allergy (dermatitis), delayed allergy, pollen allergy (hay fever), drug allergy, sting allergy, bite allergy, gastrointestinal allergy; food allergy; and physical allergy, for example cold urticaria, angioedema, cholinergic urticaria and photosensitivity.

Embodiment 30. The composition, method, process or use of any one of the preceding embodiments wherein the fructose amino acid is selected from:

(a) N2-fructopyranosylhomoarginine;
(b) Fructose homoarginine
(c) N2-ß-D-Fructopyranos-1-yl-Arginine;
(d) fructose arginine;
(e) fructose lysine
(f) fructose serine;
(g) 1-Deoxy-1-(N-γ-aminobutyric acid)fructose; and
(h) pharmaceutically acceptable salts, solvates, metabolites, prodrugs, bioisosteres, derivatives and protected forms of any one of (a)-(g).

Embodiment 31. The composition, method, process or use of any one of the preceding embodiments wherein the fructose amino acid: (a) inhibits one or more β-glucuronidases; and/or (b) inhibits one or more hexosaminidases; and/or (c) serves as a pharmacoperone for one or more β-glucuronidases; and/or (d) serves as a pharmacoperone for one or more hexosaminidases; and/or (e) inhibits the build-up and/or deposition of one or more β-glucuronidases associated with neurological disorders; and/or (f) inhibits the build-up and/or deposition of one or more hexosaminidases associated with neurological disorders; and/or (g) Interacts with one or more receptors of β-glucuronidase and/or hexosaminidases; (h) is an AGE receptor agonist; or (i) is an AGE receptor antagonist.

Other aspects and preferred embodiments of the Invention are defined and described in the claims set out below.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited Integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The phrase "consisting essentially of" is used herein to require the specified integer(s) or steps as well as those which do not materially affect the character or function of the claimed invention.

As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

As used herein, the term "fructose amino acid" (or FAA) is intended to define a compound of the formula:

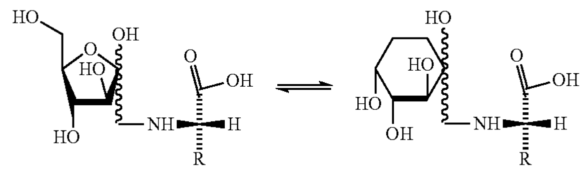

where R is any protein or non-protein amino acid side chain.

Thus, the fructose amino acids of the invention include:

(a) N2-fructopyranosylhomoarginine;
(b) N2-ß-D-Fructopyranos-1-yl-Arginine;
(c) fructose homoarginine;
(d) fructose serine; and
(e) 1-Deoxy-1-(N-γ-aminobutyric acid)fructose.

In all cases, the fructose amino acids of the invention also include pharmaceutically acceptable salts, solvates, metabolites, prodrugs, bioisosteres, derivatives and protected forms thereof. For example, as used herein, the term N2-β-D-Fructopyranos-1-yl-Arginine (5-carbamimidamido-2-{[(2,3,4,5-tetrahydroxytetrahydro-2H-pyran-2-yl)methyl]amino}pentanoic acid) is intended to define sensu stricto a compound of the formula:

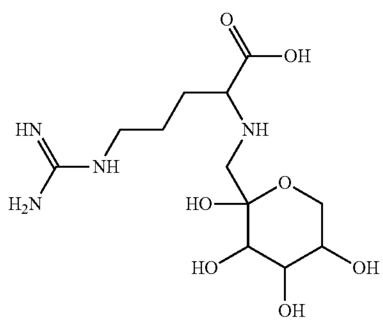 [SMILES: N=C(N)NCCCC(NCC1(O)OCC(O)C(O)C1O)C(=O)O]

but is also to be interpreted sensu lato to include pharmaceutically acceptable salts, solvates, metabolites, prodrugs, bioisosteres, derivatives and protected forms thereof.

In the case of basic amino acids the fructose may also be attached to other nitrogens such as in the N1-fructopyranosyl-arginine (2-amino-5-{N'-[(2,3,4,5-tetrahydroxytetrahydro-2H-pyran-2-yl)methyl]carbamimidamido}pentanoic acid) shown in the formula below.

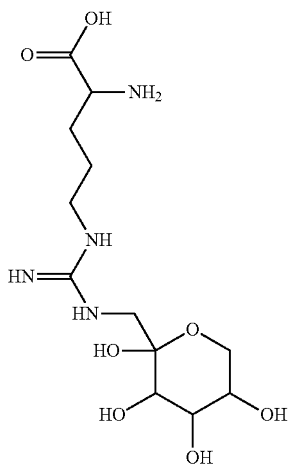 [SMILES: N=C(NCCCC(N)C(=O)O)NCC1(O)OCC(O)C(O)C1O]

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "AGE-mediated disease" defines diseases, as defined above, in which AGEs play a biological role. The role played by the AGEs may be direct or indirect and may be necessary and/or sufficient for the manifestation of the symptoms of the disease (or its aetiology or progression). Thus, AGE activity (and in particular elevated levels of AGEs caused by endogenous AGE over-production) need not necessarily be the proximal cause of the disease, state or condition: rather, it is contemplated that AGE-mediated diseases include those having multifactorial aetiologies and complex progressions in which AGEs are only partially involved. AGE-mediated diseases therefore include: inflammatory diseases; depression; neurodegenerative disorders, Including Alzheimer's disease and Parkinson's disease; diabetes; complications and clinical sequelae of diabetes; amyotrophic lateral sclerosis (ALS or Lou Gehrig's disease); muscle wasting; atherosclerosis; peripheral vascular disease; myocardial infarction; congestive heart failure; diabetic cataracts; diabetic retinopathy; diabetic neuropathy; diabetic nephropathy; ageing, swelling or erythema of the skin and psoriasis.

Cosmetic applications of the invention include the reduction of swelling and/or erythema of the skin, for example by topical application of the cosmetic compositions of the Invention to the skin.

Exemplary inflammatory diseases include: autoimmune disease, asthma, allergy, graft versus host disease; sarcoidosis; vascular inflammatory disease, including disseminated intravascular coagulation, atherosclerosis, Kawasaki's pathology; vasculitis; Sjogren's syndrome; psoriatic arthritis; enteropathic arthritis; reactive arthritis and arthritis associated with inflammatory bowel disease.

The autoimmune disease may be selected from: Grave's disease; rheumatoid arthritis; Hashimoto's thyroiditis; vitiligo; diabetes (e.g. type I diabetes or type II diabetes); pernicious anaemia; multiple sclerosis: glomerulonephritis; systemic lupus E (SLE, lupus); Sjogren syndrome; scleroderma; psoriasis; ankylosing spondiltis; myasthenia gravis; pemphigus; polymyositis; dermomyositis; uveitis; Guillain-Barre syndrome; Crohn's disease; ulcerative colitis and inflammatory bowel disease (IBD).

The allergy may be selected from: atopic allergy, allergic rhinitis, allergic conjunctivitis, atopic dermatitis, hypereosinophilia, irritable bowel syndrome, allergen-induced migraine, bacterial allergy, bronchial allergy (asthma), contact allergy (dermatitis), delayed allergy, pollen allergy (hay fever), drug allergy, sting allergy, bite allergy, gastrointestinal allergy, food allergy; and physical allergy, for example cold urticaria, angioedema, cholinergic urticaria and photosensitivity.

As used herein, the term "treatment" or "treating" refers to an intervention (e.g. the administration of an agent to a subject) which cures, ameliorates or lessens the symptoms of a disease or removes (or lessens the impact of) its cause(s) (for example, pathological AGE accumulation). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

The term "subject" (which is to be read to include "individual", "animal", "patient" or "mamma" where context permits) defines any subject, particularly a mammalian subject, for whom treatment is indicated. Mammalian subjects Include, but are not limited to, humans, domestic animals, farm animals, zoo animals, sport animals and pet animals. In preferred embodiments, the subject is a human.

The term pharmacoperone is a term of art (from "pharmacological chaperone") used to define a class of biologically active small molecules (sometimes also referred to in the art as "chemical chaperones") that serve as molecular scaffolds, causing otherwise misfolded mutant proteins to fold and route correctly within the cell.

As used herein, an effective amount of a compound or composition defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

The term "cosmetic composition" is used herein to refer to a composition suitable for topical application in humans. Such compositions therefore typically include various cosmetically-acceptable excipients or carriers. These may Include one or more agents having cosmetic properties, for example skin softeners, cleansing agents, skin emollients, perfumes, sun block or deodorants. Cosmetic compositions may be formulated, for example, as a solution, gel, lotion, cream, shampoo or a spray, for example a water-based solution, gel, lotion, cream, shampoo or spray.

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:

- compositions (e.g. unitary formulations) comprising the two or more compounds/agents in admixture (for example within the same unit dose);
- compositions comprising material in which the two or more compounds/agents are chemically/physicochemicaly linked (for example by crosslinking, molecular agglomeration or binding to a common vehicle moiety);
- compositions comprising material in which the two or more compounds/agents are chemically/physicochemicaly co-packaged (for example, disposed on or within lipid vesicles, particles (e.g. micro- or nanoparticles) or emulsion droplets);
- pharmaceutical kits, pharmaceutical packs or patient packs in which the two or more compounds/agents are co-packaged or co-presented (e.g. as part of an array of unit doses);

Examples of non-physically associated combined compounds/agents include:

- material (e.g. a non-unitary formulation) comprising at least one of the two or more compounds/agents together with instructions for the extemporaneous association of the at least one compound/agent to form a physical association of the two or more compounds/agents;
- material (e.g. a non-unitary formulation) comprising at least one of the two or more compounds/agents together with Instructions for combination therapy with the two or more compounds/agents;
- material comprising at least one of the two or more compounds/agents together with instructions for administration to a patient population in which the other(s) of the two or more compounds/agents have been (or are being) administered;
- material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above).

Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. Inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package Insert contained in the patient pack, normally missing in patient prescriptions. The inclusion of a package insert has been shown to improve patient compliance with the physician's instructions. The combinations of the invention may produce a therapeutically efficacious effect relative to the therapeutic effect of the individual compounds/agents when administered separately.

The term bioisostere (or simply isostere) is a term of art used to define drug analogues in which one or more atoms (or groups of atoms) have been substituted with replacement atoms (or groups of atoms) having similar steric and/or electronic features to those atoms which they replace. The substitution of a hydrogen atom or a hydroxyl group with a fluorine atom is a commonly employed bioisosteric replacement. Sila-substitution (C/Si-exchange) is a relatively recent technique for producing isosteres. This approach involves the replacement of one or more specific carbon atoms in a compound with silicon (for a review, see Tacke and Zilch (1986) Endeavour, New Series 10: 191-197). The sila-substituted isosteres (silicon isosteres) may exhibit improved pharmacological properties, and may for example be better tolerated, have a longer half-life or exhibit increased potency (see for example Englebienne (2005) Med. Chem., 1(3): 215-226). Similarly, replacement of an atom by one of its isotopes, for example hydrogen by deuterium, may also lead to improved pharmacological properties, for example leading to longer half-life (see for example Kushner et al (1999) Can J Physiol Pharmacol. 77(2):79-88). In its broadest aspect, the present invention contemplates all bioisosteres (and specifically, all silicon bioisosteres) of the compounds of the invention.

The terms derivative and pharmaceutically acceptable derivative as applied to the compounds of the invention define compounds which are obtained (or obtainable) by chemical derivatization of the parent compound of the invention. The pharmaceutically acceptable derivatives are therefore suitable for administration to or use in contact with the tissues of humans without undue toxicity, irritation or allergic response (i.e. commensurate with a reasonable benefit/risk ratio). Preferred derivatives are those obtained (or obtainable) by alkylation, esterification or acylation of the parent compounds. Thus, the pharmaceutically acceptable derivates of the compound of the invention includes N-oxides and esters thereof.

The pharmaceutically acceptable derivatives of the invention may retain some or all of the biological activities described herein. In some cases, the biological activity is increased by derivatization. The derivatives may act as pro-drugs, and one or more of the biological activities described herein may arise only after in vivo processing. Particularly preferred pro-drugs are ester derivatives which are esterified at one or more of the free hydroxyls and which are activated by hydrolysis in vivo. Derivatization may also augment other biological activities of the compound, for example bioavailability and/or glycosidase inhibitory profile. For example, derivatization may increase CNS penetration (e.g. penetration of the blood-brain barrier).

The term pharmaceutically acceptable salt defines any non-toxic organic or Inorganic acid addition salt of the free base which are suitable for use in contact with the tissues of humans and lower animals without undue toxicity, irritation, allergic response and which are commensurate with a reasonable benefit/risk ratio. Suitable pharmaceutically acceptable salts are well known in the art. Examples are the salts with inorganic acids (for example hydrochloric, hydrobromic, sulphuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid).

These salts and the free base compounds can exist in either a hydrated or a substantially anhydrous form. Crystalline forms, including all polymorphic forms, of the iminosugars of the invention are also contemplated and in general the acid addition salts of the compounds are crystalline materials which are soluble in water and various hydrophilic organic solvents and which in comparison to their free base forms, demonstrate higher melting points and an increased solubility.

The term pharmaceutically acceptable metabolite as applied to the compounds of the invention defines a pharmacologically active product produced through metabolism in the body of the specified compound or salt thereof.

The term pharmaceutically acceptable prodrug as applied to the compounds of the invention defines any pharmaceutically acceptable compound that may be converted under physiological conditions or by solvolysis to the specified compound, to a pharmaceutically acceptable salt of such compound or to a compound that shares at least some of the activity of the specified compound.

Prodrugs and active metabolites of the compounds of the invention may be identified using routine techniques known in the art (see for example, Bertolini et al., J. Med. Chem., 1997, 40, 2011-2016).

In the present specification the term "alky" defines a straight or branched saturated hydrocarbon chain. The term "$C_1$-$C_6$ alkyl" refers to a straight or branched saturated hydrocarbon chain having one to six carbon atoms. The term "$C_1$-$C_9$ alkyl" refers to a straight or branched saturated hydrocarbon chain having one to nine carbon atoms. The term "$C_1$-$C_{15}$ alkyl" refers to a straight or branched saturated hydrocarbon chain having one to fifteen carbon atoms. Preferred is $C_1$-$C_6$ alkyl. Examples Include methyl, ethyl, n-propyl, isopropyl, t-butyl, n-hexyl. The alkyl groups of the invention may be optionally substituted by one or more halogen atoms.

In the present specification the term "alkenyl" defines a straight or branched hydrocarbon chain having containing at least one carbon-carbon double bond. The term "$C_1$-$C_6$ alkenyl" refers to a straight or branched unsaturated hydrocarbon chain having one to six carbon atoms. The term "$C_1$-$C_9$ alkenyl" refers to a straight or branched unsaturated hydrocarbon chain having one to nine carbon atoms. The term "$C_1$-$C_{15}$ alkenyl" refers to a straight or branched unsaturated hydrocarbon chain having one to fifteen carbon atoms. Preferred is $C_1$-$C_9$ alkenyl. Examples include ethenyl, 2-propenyl, and 3-hexenyl. The alkenyl groups of the invention may be optionally substituted by one or more halogen atoms.

In the present specification the term "alkynyl" defines a straight or branched hydrocarbon chain having containing at least one carbon-carbon triple bond. The term "$C_1$-$C_6$ alkynyl" refers to a straight or branched unsaturated hydrocarbon chain having one to six carbon atoms. The term "$C_1$-$C_9$ alkynyl" refers to a straight or branched unsaturated hydrocarbon chain having one to nine carbon atoms. The term "$C_1$-$C_{15}$ alkynyl" refers to a straight or branched unsaturated hydrocarbon chain having one to fifteen carbon atoms. Preferred is $C_1$-$C_6$ alkynyl. Examples Include ethynyl, 2-propynyl, and 3-hexynyl. The alkynyl groups of the invention may be optionally substituted by one or more halogen atoms.

The term isolated as applied to the fructose amino acids of the invention is used herein to indicate that the fructose amino acids exists in a physical milieu distinct from that in which it occurs in nature (or in the case of synthetic fructose amino acids, is purified to some degree). For example, the isolated fructose amino acids may be substantially isolated (for example purified) with respect to the complex cellular milieu in which it naturally occurs (or with respect to the some or all of the starting products, intermediates, buffers, solvents, reactants and/or co-products from which it is synthesised).

When the isolated material (e.g. synthetic, non-naturally occurring fructose amino acids) is purified, the absolute level of purity is not critical and those skilled in the art can readily determine appropriate levels of purity according to the use to which the material is to be put. Preferred, however, are purity levels of 50% w/w, 60% w/w, 70% w/w, 80% w/w, 90% w/w, 99% w/w or higher. In some circumstances, the isolated fructose amino acids forms part of a composition (for example a more or less crude extract containing many other substances) or buffer system, which may for example contain other components. In other circumstances, the isolated fructose amino acids may be purified to essential homogeneity, for example as determined spectrophotometrically, by NMR or by chromatography (for example GC-MS of the trimethylsilyl-derivatives).

The term herbal medicine is used herein to define a pharmaceutical composition in which at least one active principle (e.g. the fructose amino acids) is not chemically synthesized and is a phytochemical constituent of a plant. In most cases, this non-synthetic active principle is not isolated (as defined herein), but present together with other phytochemicals with which it is associated in the source plant. In some cases, however, the plant-derived bioactive principle(s) may be in a concentrated fraction or isolated (sometimes involving high degrees of purification). In many cases, however, the herbal medicine comprises a more or less crude extract, infusion or fraction of a plant or even an unprocessed whole plant (or part thereof), though in such cases the plant (or plant part) is usually at least dried and/or milled.

The term bioactive principle is used herein to define a phytochemical which is necessary or sufficient for the pharmaceutical efficacy of the herbal medicament in which it is comprised. In the case of the present invention, the bioactive principle comprises the fructose amino acids of the invention.

The term phytochemical is used herein in a broad sense to encompass any chemical constituent of a plant, including macromolecules and small molecules. Important examples include alkaloids (for example imino sugars and imino sugars acids, e.g. selected from the structural classes pyrrolidines, piperidines, pyrrolizidine, Indolizidines, tropanes and nortropanes), carbohydrate analogues, phenolic compounds, terpenoids, enzyme inhibitors, glycosides, nucleotides, amino acids, lipids and sugars.

The term nutraceutical is used herein to define a food product (or isolate thereof) which provides physiological benefits or protects against disease. Preferred nutraceuticals of the invention are anti-inflammatory.

The term standard specification is used herein to define a characteristic, or a phytochemical profile, which is correlated with an acceptable quality of the herbal medicine, cosmetic or nutraceutical. In this context, the term quality is used to define the overall fitness of the product for its intended use, and includes the presence of fructose amino acids at an appropriate concentration.

In its broadest aspect, the present invention contemplates all optical isomers, racemic forms and diastereomers of the fructose amino acids of the invention. Those skilled in the art will appreciate that, owing to the asymmetrically substituted carbon atoms present in the fructose amino acids of the invention, the fructose amino acids of the invention may exist and be synthesised and/or isolated in optically active and racemic forms. Thus, references to the fructose amino acids of the present Invention encompass the fructose amino acids as a mixture of diastereomers, as individual diastereomers, as a mixture of enantiomers as well as in the form of Individual enantiomers.

Therefore, the present invention contemplates all optical isomers and racemic forms thereof of the fructose amino acids of the invention, and unless Indicated otherwise (e.g. by use of dash-wedge structural formulae) the compounds shown herein are intended to encompass all possible optical isomers of the compounds so depicted. In cases where the stereochemical form of the fructose amino acids is important for pharmaceutical utility, the invention contemplates use of an isolated eutomer. Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation.

Biological Activities and Functional Attributes of the Fructose Amino Acids of the Invention Without wishing to be bound by any theory, the fructose amino acids of the invention may:

(a) inhibit β-glucuronidases and/or hexosaminidases; and/or
(b) serve as pharmacoperones for β-glucuronidases and/or hexosaminidases; and/or
(c) inhibit the build-up and/or deposition of β-glucuronidases or hexosaminidases in neurological disorders; and/or
(d) interact with receptors of β-glucuronidase and/or hexosaminidases; and/or
(e) act as agonists or antagonists of AGE receptors.

Posology

The compounds of the present invention can be administered topically or by oral or parenteral routes, Including intravenous, Intramuscular, intraperitoneal, subcutaneous, transdermal, airway (aerosol), rectal, vaginal and topical (including buccal and sublingual) administration.

The amount administered can vary widely according to the particular dosage unit employed, the period of treatment, the age and sex of the patient treated, the nature and extent of the disorder treated, and the particular compound selected.

Moreover, the compounds of the invention can be used in conjunction with other agents known to be useful in the treatment of diseases or disorders arising from protein folding abnormalities (as described Infra) and in such embodiments the dose may be adjusted accordingly.

In general, the effective amount of the compound administered will generally range from about 0.01 mg/kg to 500 mg/kg daily. A unit dosage may contain from 0.05 to 500 mg of the compound, and can be taken one or more times per day. The compound can be administered with a pharmaceutical carrier using conventional dosage unit forms either orally, parenterally, or topically, as described below.

The preferred route of administration is oral administration. In general a suitable dose will be in the range of 0.01 to 500 mg per kilogram body weight of the recipient per day, preferably in the range of 0.1 to 50 mg per kilogram body weight per day and most preferably in the range 1 to 5 mg per kilogram body weight per day.

The desired dose is preferably presented as a single dose for daily administration. However, two, three, four, five or six or more sub-doses administered at appropriate intervals throughout the day may also be employed. These sub-doses may be administered in unit dosage forms, for example, containing 0.001 to 100 mg, preferably 0.01 to 10 mg, and most preferably 0.5 to 1.0 mg of active ingredient per unit dosage form.

Formulation

The compound for use according to the invention may take any form. It may be synthetic or isolated from natural sources (for example from any of the botanical sources identified herein, including for example a botanical source selected from plant species *Hypericum performatum* (St John's wort), *Andrographis paniculata, M. chamomilla* (Chamomile), *Conopodium majus* (Pignut), *Solanum tuberosum* (potato), *Stevia rebaudiana, Lycium chinense/Lycium barbarum* (Goji), *Angelica archangelica* and *Cissus quadrangularis*.

When isolated from a natural source, the fructose amino acids may be purified. However, the compositions of the invention may take the form of herbal medicines, as hereinbefore defined. Such herbal medicines preferably are analysed to determine whether they meet a standard specification prior to use.

The herbal medicines for use according to the Invention may be dried plant material. Alternatively, the herbal medicine may be processed plant material, the processing involving physical or chemical pre-processing, for example powdering, grinding, freezing, evaporation, filtration, pressing, spray drying, extrusion, supercritical solvent extraction and tincture production. In cases where the herbal medicine is administered or sold in the form of a whole plant (or part thereof), the plant material may be dried prior to use. Any convenient form of drying may be used, including freeze-drying, spray drying or air-drying.

Fructose amino acids may be separated from the higher molecular weight components such as proteins and polysaccharides by using various membrane technologies. These include microfiltration, ultrafiltration and nanofiltration. Alternatively, or in addition, electrodialysis may also be used to concentrate the charged fructose amino acids. These methods use membranes of pore sizes that allow only molecules below a certain size to pass or rely on charges on the molecules to allow or not allow them to pass through the membrane. Anion and cation exchange resins may also be used to concentrate the fructose amino acids.

When isolated from a natural source, the compound for use according to the invention may be purified. In embodiments where the compound is formulated together with a pharmaceutically acceptable excipient, any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc.

The pharmaceutical compositions may take any suitable form, and include for example tablets, elixirs, capsules, solutions, suspensions, powders, granules and aerosols.

The pharmaceutical composition may take the form of a kit of parts, which kit may comprise the composition of the invention together with instructions for use and/or a plurality of different components in unit dosage form.

Tablets for oral use may Include the compound for use according to the invention, mixed with pharmaceutically acceptable excipients, such as inert diluents, disintegrating agents, binding agents, lubricating agents, sweetening agents, flavouring agents, colouring agents and preservatives. Suitable Inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the compound for use according to the invention is mixed with a solid diluent, and soft gelatin capsules wherein the active Ingredient is mixed with water or an oil such as peanut oil, liquid paraffin or olive oil.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the Invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

For oral administration the compound can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch.

In another embodiment, the compounds of the invention are tableted with conventional tablet bases such as lactose, sucrose, and cornstarch in combination with binders such as acacia, cornstarch, or gelatin, disintegrating agents Intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, colouring agents, and flavouring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The compounds of the Invention may also be administered parenterally, that is, subcutaneously, intravenously, intramuscularly, or intraperitoneally.

In such embodiments, the compound is provided as injectable doses in a physiologically acceptable diluent together with a pharmaceutical carrier (which can be a sterile liquid or mixture of liquids). Suitable liquids include water, saline, aqueous dextrose and related sugar solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as poly(ethylene-glycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carhomers, methylcellulose, hydroxypropylmethylcellulose, or carboxymethylcellulose), or emulsifying agent and other pharmaceutically adjuvants.

Suitable oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids Include oleic acid, stearic acid, and isostearic acid. Suitable fatty acid esters are, for example, ethyl oleate and isopropyl myristate.

Suitable soaps include fatty alkali metal, ammonium, and triethanolamine salts and suitable detergents include cationic detergents, for example, dimethyl dialkyl ammonium halides, alkyl pyridinium halides, and alkylamines acetates: anionic detergents, for example, alkyl, aryl, and olefin sulphonates, alkyl, olefin, ether, and monoglyceride sulphates, and sulphosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the compound for use according to the invention in solution. Preservatives and buffers may also be used. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compound for use according to the invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the compound from about 0.1 to about 10% w/v (weight per unit volume).

When used adjunctively, the compound for use according to the invention may be formulated for use with one or more other drug(s). Thus, adjunctive use may be reflected in a specific unit dosage designed to be compatible (or to synergize) with the other drug(s), or in formulations in which the compound is admixed with one or more enzymes.

Adjunctive uses may also be reflected in the composition of the pharmaceutical kits of the invention, in which the compounds of the invention is co-packaged (e.g. as part of an array of unit doses) with the enzymes. Adjunctive use may also be reflected in information and/or instructions relating to the co-administration of the compound and/or enzyme.

Cosmetic Formulations

The cosmetic compositions of the invention may be selected for example from moisturizing compositions, cleansing compositions, or any composition that may provide a benefit to the skin. The cosmetic compositions of the invention may comprise cosmetically-acceptable excipients or carriers, for example selected from those described below.

In one embodiment, the cosmetic composition is a cleansing composition. Suitable cleansing compositions are solid or semi-solid at room temperature. Examples of useful cleansing compositions include, but are not limited to, fatty acid soaps, including glycerin soaps, synthetic detergents and mixtures thereof. Solid cleansing compositions are extensively taught in Soap Technology for the 1990's, the contents of which are incorporated herein by reference. It is desirable that the cleansing composition be flowable.

In one embodiment of the Invention, the cleansing composition comprises glycerin soap. Examples of glycerin soaps useful in the present invention include but are not limited to those disclosed in U.S. Pat. Nos. 4,405,492 and 4,879,063, the disclosures of which are hereby Incorporated by reference.

Examples of suitable fatty acid soaps include soaps derived from hydrocarbon chain lengths of from approximately 10 to 22 (including carboxyl carbon) and may be saturated or unsaturated. The soap may be, for example, the sodium salt, potassium salt, ammonium salt, triethanolammonium salt and mixtures thereof.

Suitable synthetic detergents include those known in the art for the desired purpose. Examples of detergents useful for personal cleansing include the isethionates, sarcosinates, and glyceryl ether sulfonates which may be pure chain length variants or those derived from commercial oils such as coconut oil. Other suitable detergents include anionic acyl sarcosinates, methyl acyl taurates. N-acyl glutamates, alkyl sulphosuccinates, alkyl phosphate esters, ethoxylated alkyl phosphate esters, trideceth sulphates, protein condensates, mixtures of ethoxylated alkyl sulphates and alkyl amine oxides, betaines, sultaines and mixtures thereof. Included are the alkyl ether sulphates with 1 to 12 ethoxy groups, especially ammonium and sodium lauryl ether sulphates.

The cosmetic composition may be a moisturizing composition.

Other optional components of the cosmetic compositions of the Invention Include, but are not limited to, perfumes, fragrances, preservatives, colourants, dyes, anti-caking agents, and personal care ingredients, including, but are not limited to, skin and hair care Ingredients.

Examples of suitable personal care ingredients useful in the present invention include but are not limited to safe and effective amounts of: humectants, sunscreen actives, skin soothers, anti-irritants, anti-inflammatories, emollients, conditioning agents, moisturizers, deodorants, anti-perspirants, artificial tanning agents, antimicrobial agents, anti-acne agents, anti-wrinkle agents, anti-skin atrophy agents, skin firming agents, anti-itch agents, anti-fungal agents, topical anaesthetics, skin tone evening agents, active natural ingredients, agents for minimizing the appearance or retarding regrowth of unwanted hair, skin texture modifiers, and additional cleansing agents.

In one embodiment the fructose amino acids may be used from a water or alcoholic water extract by using a water in oil (w/o) emulsion such as are employed for example in the treatment of dry skin and emollient applications Emollients function by their ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 cetyl ether, steareth-10, oleth-8, PPG-4 lauryl ether, vitamin E acetate, PEG-7 glyceryl cocoate, lanolin, and combinations thereof. Vitamin E acetate, PEG-7 glyceryl cocoate and combinations thereof are preferred.

Examples of suitable humectants include polyhydric alcohols. Suitable polyhydric alcohols include, but are not limited to, glycerol (also known as glycerin), polyalkylene glycols, alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof.

Suitable skin soothers include, but are not limited to, panthenol, bisabolol, allantoin, aloe, and combinations thereof.

Suitable conditioning agents include, but are not limited to, dimethicone propyl PG-betaine, dimethicone copolyols, polyquaternium-10, guar, guar derivatives, and combinations thereof. Suitable anti-acne active ingredients include, but are not limited to, salicylic acid, sulphur, lactic acid, glycolic acid, pyruvic acid, urea, resorcinol, N-acetylcysteine, retinoic acid, benzoyl peroxide, octopirox, triclosan, azelaic acid, phenoxyethanol, phenoxypropanol, flavonoids, derivatives thereof, and combinations thereof. Salicylic acid and benzoyl peroxide are preferred.

Quality Control Aspects

Food Additive Samples

The food additive samples used in the methods of the present invention may be dried plant material or aliquots of the herbal food additive in the form in which it is added to foodstuffs and beverages. Alternatively, the samples may be pre-processed in any of a wide variety of ways prior to characterization. Pre-processing may involve physical or chemical pre-processing, for example powdering, grinding, freezing, evaporation, filtration, pressing, spray drying, extrusion, supercritical solvent extraction and tincture production.

Preferably, the food additive sample is fractionated prior to characterization. Any suitable method of fractionation may be employed, including solvent extraction(s). In a preferred embodiment the sample is fractionated by: (a) ion-exchange chromatography to produce an extract enriched in polar compounds and a non-polar residue; and then (b) chromatographic fractionation of the enriched extract of step (a) to yield one or more polar fractions comprising one or more polar phytochemical(s). In such embodiments the chromatographic fractionation preferably comprises gas-liquid chromatography (GC), for example GC-MS. When GC is used, the enriched extract may be derivatized prior to chromatography.

In cases where the herbal food additive is administered or sold in the form of a whole plant (or part thereof), the plant material may be dried prior to use. Any convenient form of drying may be used, including freeze-drying, spray drying or air-drying.

Detection of Fructose Amino Acids

Any suitable form of characterization of the food additive sample may be employed, including without limitation functional and/or physical and/or chemical characterization, sufficient to detect the presence or absence or measure the amount of FAAs in the sample.

Where the samples are physically characterized, the characterization may be selected from: (a) quantification of the phytochemical component(s); and/or (b) measurement of the purity of the constituents; and/or (c) determination of molecular weight (or molecular weight distribution or various statistical functions thereof in the case of fractions which comprise a plurality of different phytochemical constituents); and/or (d) determination of the molecular formula (e) (e.g. by nuclear magnetic resonance); and/or (e) spectral analysis.

Spectral analysis is particularly preferred, and may produce any or all of the following spectra:

(a) mass spectra (e.g. the mass to charge (m/z) value versus abundance), and/or
(b) chromatographic data (e.g. spectra, column retention times, elution profiles etc), and/or
(c) photodiode array (PDA) spectra (e.g. in both UV and visible ranges), and/or
(d) electrochemical detection
(e) nuclear magnetic resonance (NMR) spectra (e.g. spectral data sets obtained via $^1H$ and/or $^{13}C$ NMR).

When used according to the invention, the spectral analysis may be coupled with fractionation of the sample, for example by use of GC-MS and/or HPLC-PDA-MS.

Particularly preferred is the use of GC-MS to detect the presence or absence or measure the amount of FAA in the sample.

Where the samples are chemically characterized, the characterization may be selected from measurements of the chemical reactivity of phytochemical constituent(s), the solubility of phytochemical constituent(s), the stability and melting point of phytochemical constituent(s) or any combination thereof.

Where the samples are functionally characterized, the characterization may comprise a biological assay, for example selected from in vivo or in vitro assays, enzyme Inhibition assays (for example glycosidase and/or lipase inhibition), receptor binding assays, cellular assays (e.g. cell replication, cell-pathogen, cell-cell interaction and cell secretion assays), immunoassays, anti-microbial activity (e.g. bacterial and viral cell-binding and/or replication) assays, toxicity assays (e.g. $LD_{50}$ assays) or any combination thereof.

Solvent Extractions

Suitable polar solvents for use in the process of the invention Include without limitation organic solvents such as organic alcohols. Preferred are ethanol and methanol, as well as ethanol/water or methanol/water mixtures. Preferably, the polar solvent is selected from 51 to 80% ethanol/water, 31 to 50% ethanol/water, and up to 30% ethanol/water. Particularly preferred is a polar solvent which is approximately 50% ethanol/water. Suitable non-polar solvents for use in the process of the invention include without limitation organic solvents such as hexane and dichloromethane (DCM) or chloroform. Particularly preferred is dichloromethane. The conditions (time, temperature, degree of agitation etc.) under which the extraction(s) are performed can be readily determined empirically and vary according to the nature of the sample, the nature of any pre-processing and the solvent system selected.

Chromatographic Fractionation

Chromatographic fractionation may comprise gas-liquid chromatography. Gas-liquid chromatography is a process whereby a complex mixture of volatile substances is separated into its constituents by partitioning the sample between an inert gas under pressure and a thin layer of non-volatile liquid coated on an inert support inside a heated column. In order to achieve a good separation of specific compounds in a mixture, it is crucial to use a column with the correct characteristics. The nature of the solid support, type and amount of liquid phase, method of packing, overall length and column temperature are Important factors.

Those skilled in the art, by routine trial and error and by using common general knowledge, will be able readily to determine the appropriate column characteristics according to the circumstances, including inter alia the extract under study and the nature of the solvent used in the extraction and the types of chemicals expected in those solvents. Particularly preferred, and useful in many circumstances, are capillary columns coated with a non-polar liquid phase (25 m×0.22 mm id×0.25 μm BPX5 stationary phase, produced by SGE Ltd., or equivalents thereof).

Many compounds are unsuitable for direct injection into a gas chromatograph because of their high polarity, low volatility or thermal Instability. Compounds that are highly hydroxylated are difficult to vapourise because of inter-molecular hydrogen bonding. However, by replacing the hydroxyl hydrogens with other chemical groups, they can be made sufficiently volatile for GC analysis. The two most popular means of derivatising hydroxyl groups are acetylation and silylation, where acetylates [$CH_3CO—O—R$] or silyl ethers, e.g. trimethylsilyl (TMS) ethers [$(CH_3)_3Si—O—R$] are formed. Thus, in embodiments where the enriched extract is chromatographically fractionated on an analytical scale the phytochemical constituents of the enriched extract are preferably derivatized, for example by acylation or silylation. Particularly preferred is trimethyl silyl (TMS) derivatization.

Chromatographic fractionation may also comprise ion exchange chromatography. Ion-exchange chromatography partially purifies ionic species to concentrate them and remove contaminating substances. Those skilled in the art, by routine trial and error and using common general knowledge, will be able readily to identify suitable column packing materials and mobile phase(s), which will depend inter alia on the quantities to be fractionated, the extracts under study and the nature of the solvent used in the extraction. Particularly preferred in the methods of the present Invention are strongly acidic cation exchange resins which can be used in either the free acid or hydrogen (H) form or in the ammonium ($NH_4^+$) salt form). These forms adsorb cations from solution and release an equivalent number of counter-Ions back into solution (either $H^+$ or $NH_4^+$ ions, depending on the form used).

Fraction Characterization

The form the characterization takes depends on the nature of the herbal food additive under study and the characterization techniques employed. In general, any or all of the following approaches may be used:

(a) Functional Characterization

The functional characterization may comprise a biological assay. Biological assays may be carried out in vivo or In v/to, and may include enzyme inhibition assays. Other biological assays include receptor binding assays, cellular assays (including cell replication, cell-pathogen and cell-cell interaction and cell secretion assays), immunoassays, anti-microbial activity (e.g. bacterial and viral cell-binding and/or replication) assays and toxicity assays (e.g. $LD_{50}$ assays).

Functional characterization may also be carried out indirectly by a form of characterization which permits the identification of one or more indices of biological activity.

(b) Physical Characterization

This can take the form of quantification of the phytochemical component(s) present in any given fraction or at any other stage in the process, measurement of the purity of the constituents, determination of molecular weight (or molecular weight distribution or various statistical functions thereof in the case of fractions which comprise a plurality of different phytochemical constituents), determination of the molecular formula(e) (e.g. by nuclear magnetic resonance) and various spectral analyses.

Particularly useful spectral characteristics include:

Mass spectra (e.g. the mass to charge (m/z) value versus abundance), and/or

Chromatographic data (e.g. spectra, column retention times, elution profiles etc), and/or Photodiode array (PDA) spectra (e.g. in both UV and visible ranges), and/or Nuclear magnetic resonance (NMR) spectra (including spectral data sets obtained via $^1H$ and/or $^{13}C$ NMR).

Spectral characterization can be coupled with the fractionation step. For example, GC-MS and HPLC-PDA-MS can be used (as described herein) to couple the fractionation with the obtention of mass spectral, UV-visible spectral and chromatographic spectral data.

Any or all of the above characteristics can be used to define a "chemical fingerprint" for any given sample (or any fraction or phytochemical constituent thereof).

(c) Chemical Characterization

This can take the form of measurements Inter all of the chemical reactivity of phytochemical constituent(s), their solubility, stability and melting point.

EXEMPLIFICATION

The invention will now be described with reference to specific Examples. These are merely exemplary and for Illustrative purposes only: they are not intended to be limiting in any way to the scope of the monopoly claimed or to the invention described. These examples constitute the best mode currently contemplated for practicing the invention.

Example 1: Identification of Fructose Amino Acids in St John's Wort Products The active components in St John's wort are widely considered to be the aromatic compounds hypericin and hyperforin and many products are standardised on these "marker" compounds. There has been debate in the scientific literature for many years over the importance of these compounds in the overall clinical activity of *Hypericum* extracts. Our analysis of St John's wort products shows the unexpected presence of significant amounts of fructose amino acids which have not previously been reported in the literature.

60 Solgar capsules each containing 300 mg raw St John's wort herb powder and 175 mg standardised St Johns wort herb powdered extract were opened and the contents extracted in 50% aq. ethanol for 15 hours. 90 Natures Aid St John's wort tablets each containing 500 mg of extract standardised to provide 1.5 mg of hypericin were similarly extracted after crushing. Each extract was filtered and the filtrate applied to the cation exchange resin Dowex 50 resin in the $H^+$ form in a column (2×30 cm). The column was washed with distilled water and the unretained material discarded. The retained material was displaced with 2M ammonium hydroxide solution and concentrated by rotary evaporation and freeze drying. Both retained samples provided 200 mg of retained compounds. On analysis by GC-MS of the trimethylsilylated retained material, major components were observed which matched fructose amino acids and not previously reported from *Hypericum* species. The compounds had characteristic mass spectra using the GC-MS method described below with major ions 217, 257, 307, 502, 520 and 574, 590 amu. Further purification of these fructose amino acids was achieved using the strongly basic anion exchange resin CG400 in the acetate form to which they were not retained and they were removed using distilled water. Fractionation was monitored by GC-MS. Further purification was conducted using the weakly acidic cation exchange resin CG50 in the ammonium form to which the compounds were also not retained. The main pure compound (20 mg yield) was submitted to proton and carbon NMR and characterised as fructopyranosyl-arginine. Those practiced in the art will be able to use similar methods to provide a fructose amino acids-enriched fraction or pure compounds.

GC-MS

All samples from ion exchange columns were freeze dried before derivatization. Trimethylsilyl (TMS) derivatives were prepared using a mixture of hexamethyldisilazane and trimethylchlorosilane in pyridine (Pierce 'Tri-Sil' silylation reagent, HMDS:TMCS:pyridine in a ratio of 2:1:10). Samples were heated at 60° C. for 15 minutes and then left at room temperature for at least 60 min. Insoluble reaction products were sedimented by centrifugation, and the supernatant was transferred to fresh vials using a syringe.

Analysis was carried out by GC-MS using a Perkin Elmer Autosystem XL gas chromatograph with a high polarity fused-silica column (Varian 'Factor Four' VF-5 ms column, 25 m×0.25 mm i.d., 0.25 μm phase thickness). The carrier gas (helium) flow rate was 1 ml min-1. Trimethylsilyl-(TMS) derivatives were separated using a temperature programme that started at 180° C. for 5 min, followed by a linear increase to 300° C. at a rate of 10° C. min-1. Electron impact mass spectrometry of the column eluant was carried out using a Perkin Elmer TurboMass Gold mass spectrometer, with a quadrupole ion filter system, which was run at 250° C. constantly during analysis. The injection volume was 1 μl.

Fructose amino acids give distinctive mass spectra as the trimethylsilyl-derivatives with major fragments seen typically at 147, 171, 300, 301, 304, 319, 520 or 574 amu. They are clearly distinguishable in the plant extracts at concentrations comparable to the primary amino acids such as aspartic acid. Using the GC method described fructose amino acids have longer retention times than the common amino acids seen at 3-5 minutes. The retention time of fructose amino acids are typically between those of the trimethylsilyl-derivatives of glucose and sucrose. The removal of common sugars by the Ion exchange methods described allows the determination of the fructose amino acids by GC-MS.

Example 2: Identification of N2-Fructopyranosylhomoarginine in Chamomile Tea

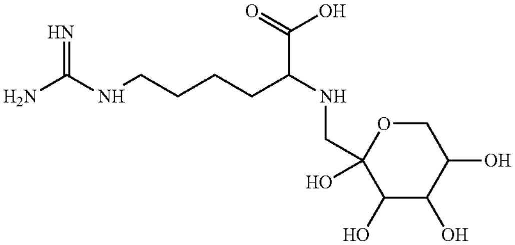 [SMILES: N=C(N)NCCCCC(NCC1(O)OCC(O)C(O)C1O)C(=O)O]

100 g of pure Chamomile flower tea was extracted in 50% aq. ethanol for 15 hours and then filtered. The filtrate was applied to the cation exchange resin Dowex 50 resin in the $H^+$ form in a column (2×50 cm). The column was washed with distilled water and the unretained material discarded. The retained material was displaced with 2M ammonium hydroxide solution and concentrated by rotary evaporation and freeze drying. Fructose amino acids could be detected by distinctive ions seen at 217, 247, 300 390, 480 and 568 amu.

Example 3. Determination of N2-beta-D-Fructopyranos-1-yl-Arginine from St John's Wort by NMR $^1H$ NMR and $^{13}C$ NMR spectra were recorded on a Bruker DRX500. Chemical shifts were expressed in parts per million with the water peak used for referencing.

N2-beta-D-Fructopyranos-1-yl-Arginine

1H NMR (500 MHz, $D_2O$) δ ppm 1.56-1.62 (4H, m, $2{\times}CH_2$), 2.71-2.77 (2H, m, $CH_2$), 3.06 (2H, m, $CH_2$), 3.14 (1H, m), 3.66 (1H, dd, J=1.5, 4 Hz), 3.66-4.00 (2H, m, $CH_2$), 3.79 (1H, m), 3.89 (1H, m). $^{13}C$ NMR (500 MHz, $D_2O$) δ ppm 24.4 ($CH_2$), 28.9 ($CH_2$), 40.7 ($CH_2$), 52.6 ($CH_2$), 63.3 (CH), 63.4 ($CH_2$), 69.0 (CH), 69.3 (CH), 69.6 (CH), 100 (C), 158.7 (C), 179.6 (C=O).

Compounds appearing similar in mass spectral fragmentation to N2-fructopyranosyl arginine were also observed in St John's wort but not isolated for full structural determination but they could be arginine with fructose attached to different nitrogens such as shown in the formulae below:

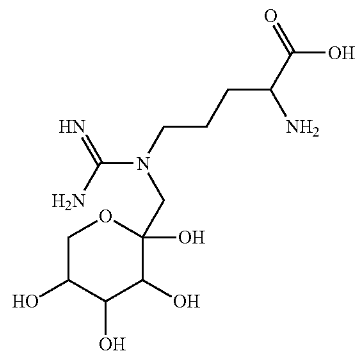

-continued

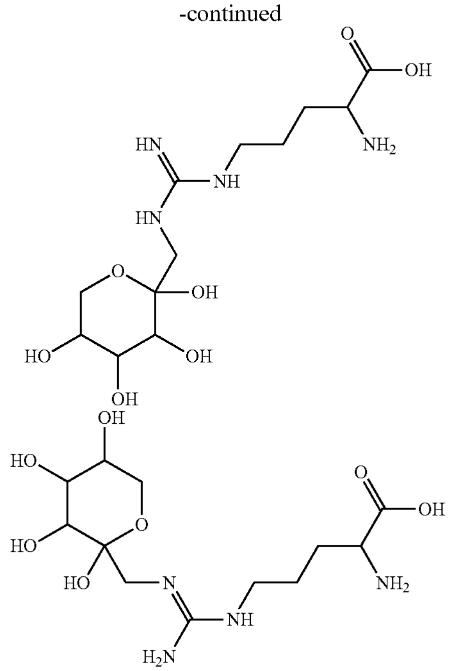

*Cissus quadrangularis* and Chamomile also contained a compound with a close mass spectral fragmentation to fructose arginine but showing one extra $CH_2$ making it a fructose homoarginine.

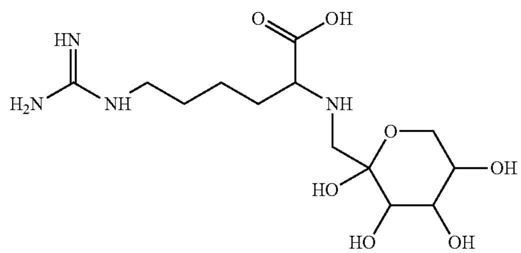 [SMILES: N=C(N)NCCCCC(NCC1(O)OCC(O)C(O)C1O)C(=O)O]

Example 4: Isolation of Other Fructose Amino Acids

Using the methods described above we have purified and identified other fructose amino acids such as:

Fructose serine from *Stevia rebaudiana* leaves.

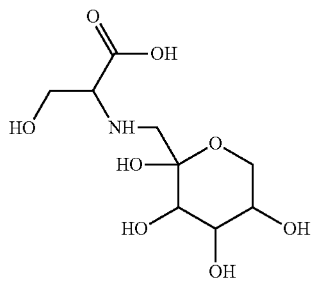 [SMILES: O=C(O)C(CO)NCC1(O)OCC(O)C(O)C1O]

1-Deoxy-1-(N-γ-aminobutyric acid)fructose (3-hydroxy-2-{[(2,3,4,5-tetrahydroxytetrahydro-2H-pyran-2-yl)methyl]amino}propanoic acid) from *Conopodium majus* (pignut) leaves. The compound is also reported from cured tobacco leaves and from stored apricots and peaches.

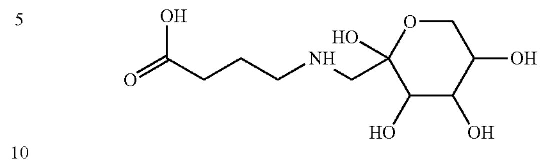

Example 5: Glycosidase Assays

All enzymes and para-nitrophenyl substrates were purchased from Sigma, with the exception of beta-mannosidase which came from Megazyme. Enzymes were assayed at 27° C. in 0.1M citric acid/0.2M disodium hydrogen phosphate buffers at the optimum pH for the enzyme. The incubation mixture consisted of 10 μl enzyme solution, 10 μl of 1 mg/ml aqueous solution of sample and 50 μl of the appropriate 5 mM para-nitrophenyl substrate made up in buffer at the optimum pH for the enzyme. The reactions were stopped by addition of 70 μl 0.4M glycine (pH 10.4) during the exponential phase of the reaction, which had been determined at the beginning using uninhibited assays in which water replaced inhibitor. Final absorbances were read at 405 nm using a Versamax microplate reader (Molecular Devices). Assays were carried out in triplicate, and the values given are means of the three replicates per assay. The method was carried out as described in Watson t al. (1997) Phytochemistry 4(2): 255-259.

The table below shows the percentage inhibition caused by fructose amino acids when tested on a panel of glycosidases at 0.2 mM. A negative value suggests a stabilisation of the enzyme or promotion of the enzyme activity (perhaps by binding to a non-catalytic site).

| Enzyme | Source | N2-β-D-Fructopyranos-1-yl-Arginine | 1-Deoxy-1-(N-γ-aminobutyric acid) fructose |
|---|---|---|---|
| α-D-giucosidase | *Saccharomyces cerevisiae* | −1.4 | −4.2 |
| α-D-glucosidase | *Bacillus sterothermophilus* | −1.7 | 0.7 |
| α-D-glucosidase | Rice (*Oryza sativa*) | −6 | −4.2 |
| β-D-glucosidase | Almond (*Prunus* sp.) | 7.6 | −0.9 |
| α-D-galactosidase | Green coffee bean (*Coffea* sp.) | 3.4 | −7.1 |
| β-D-galactosidase | Bovine liver | −3.9 | 1.3 |
| α-L-fucosidase | Bovine kidney | −9.3 | −1.3 |
| α-D-mannosidase | Jack bean (*Canavalia ensiformis*) | 35.2 | −6.2 |
| β-D-mannosidase | *Cellullomonas fimi* | −8.1 | −10.3 |
| Naringinase | *Penicillium decumbens* | 4.1 | 0.2 |
| N-acetyl-β-D-glucosaminidase | Bovine kidney | 88.5 | 55.3 |
| N-acetyl-β-D-glucosaminidase | Jack bean | −0.8 | −6.3 |
| N-acetyl-β-D-hexosaminidase | *Aspergillus oryzae* | −15.3 | −19.2 |
| Amyloglucosidase | *Aspergillus niger* | 15 | −2.9 |
| β-glucuronidase | Bovine liver | 85.2 | −1.2 |
| β-glucuronidase | *E. coli* | −9 | −0.8 |

N2-β-D-Fructopyranos-1-yl-Arginine has an $IC_{50}$ against the bovine β-glucuronidase of 101 μM and 7.7 μM against the bovine hexosaminidase. 1-Deoxy-1-(N-γ-aminobutyric acid)fructose was more weakly inhibitory to the bovine hexosaminidase with an $IC_{50}$ of 200 μM.

Example 6: Maltose Loading Test with Fructo-Arginine

The animal experimental protocols in this study were approved by the Animal Experiments Committee of the University of Toyama (S-2010 UH-2). Male ddy mice (29-33 g) after an overnight fast were used for acute disaccharide loading tests. Maltose (2.5 g/kg body weight) or Sucrose (2.5 g/kg body weight) as well as the test samples were dissolved in 0.9% NaCl solution and administered to mice via a stomach tube. A control group was loaded with saline only. Blood samples for glucose measurements were obtained from the tall vain at 0, 15, 30, 60, and 120 min after disaccharide-loading. The blood glucose levels were measured by a portable kit, Antsence II™ (Sankyo Co. Ltd. Tokyo, Japan).

The results are shown in FIG. 1, which shows the effects of N2-beta-D-Fructopyranos-1-yl-Arginine (900156) extracts on blood glucose levels. Blood glucose concentrations of male ddy mouse after an oral load with maltose, 2.5 g/kg body weight, with 500 mg/kg body weight test compound (●) or with saline (○). Each value represents the mean±SEM (n=5).

Example 7: Glycogen Phosphorlyase

N2-beta-D-Fructopyranos-1-yl-Arginine and 1-Deoxy-1-(N-γ-aminobutyric acid)fructose were tested on glycogen phosphorylase and found to give weak inhibition (14.2 and 5.5% respectively at 400 μM.

Materials. Phosphoglucomutase, glucose-8-phosphate dehydrogenase, glucose-1,6-bisphosphate, glycogen phosphorylase b, α-D-glucose 1-phosphate dipotassium salt hydrate were purchased from Sigma-Aldrich Fine Chemicals (St. Louis, Mo, USA). Glycogen and caffeine were purchased from Nacalai Tesque (Kyoto, Japan). Other chemicals were from Wako Pure Chemical industries (Osaka, Japan).

Measurement of GPb activity. GPb activity was measured in the direction of glycogenolysis using 2 mg/mL glycogen as the substrate in 45 mM phosphate buffer at pH 6.8, containing 0.1 mM EDTA. 0.34 mM $NADP^+$, 4 mM glucose-1,6-bisphosphate, 15 mM magnesium chloride, 1 mM AMP, phosphoglucomutase (0.8 units/mL), glucose 6-phosphate (glucose-6-P) dehydrogenase (3 units/mL) and glycogen phosphorylase b. The rate of enzyme-catalysed reaction in the medium can be followed as the increase in absorbance at 340 nm and 25° C. due to the formation of NADPH. GPb activity was also measured in the direction of glycogen synthesis using 25 mM glucose-1-P as substrate in a 250 mM Tris-malate buffer (pH 6.8), containing 5 mg/mL glycogen, 1 mM AMP, 15 mM cysteine, and glycogen phosphorylase b. The assay mixture was Incubated at 25° C. for 15 min and reaction was stopped by adding 250 mM sulphuric acid. Pi was measured by the Fiske-Subbarow method. The rate of enzyme-catalysed reaction in the medium was followed as the Increase in absorbance at 660 nm.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method for treating an AGE-mediated disease comprising administering an effective amount of a composition comprising an isolated fructose amino acid, said fructose amino acid being N2-b-D-Fructopyranos-1-yl-Arginine (5-carbamimidamido-2-{[(2,3,4,5-tetrahydroxytetrahydro-2H-pyran-2-yl)methyl]amino}pentanoic acid) of the formula:

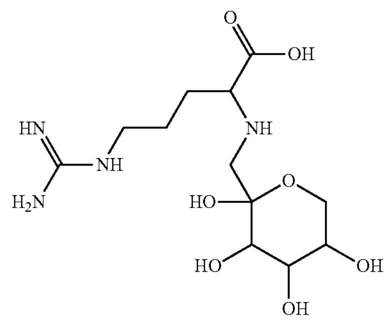 [SMILES: N=C(N)NCCCC(NCC1(O)OCC(O)C(O)C1O)C(=O)O]

or a pharmaceutically acceptable salt thereof, to a human in need thereof, wherein the isolated fructose amino acid is present in the composition at a level of at least 5% w/w, 10% w/w; 15% w/w; 20% w/w; 25% w/w; 30% w/w; 35% w/w; 40% w/w; 45% w/w; 50% w/w, 60% w/w, 70% w/w, 80% w/w, 90% w/w, or 99% w/w (on a dry weight basis).

2. The method of claim 1, wherein the composition is in a tablet, elixir, capsule, pill, troche, lozenge, melt, soap, spray, emulsion, ointment, gel, lipid vesicle, liposome, microparticle, nanoparticle, aerosol, suppository, pessary, tampon, cream, paste, foam, inhaler or syringe.

3. The method of claim 1, wherein the AGE-mediated disease is an inflammatory disease; depression; neurodegenerative disorder; Alzheimer's disease; Parkinson's disease; diabetes; complication and clinical sequelae of diabetes; amyotrophic lateral sclerosis; muscle wasting; atherosclerosis; peripheral vascular disease; myocardial infarction; congestive heart failure; diabetic cataracts; diabetic retinopathy; diabetic neuropathy; diabetic nephropathy; or swelling or erythema of the skin and psoriasis.

4. The method of claim 3, wherein the AGE-mediated disease is diabetes; complication and clinical sequelae of diabetes; diabetic cataracts; diabetic retinopathy; diabetic neuropathy; or diabetic nephropathy.

5. The method of claim 4, wherein the AGE-mediated disease is type I diabetes or type II diabetes.

* * * * *